United States Patent [19]

McAleer et al.

[11] 4,293,538

[45] Oct. 6, 1981

[54] ASSAY FOR HEPATITIS A ANTIGEN

[75] Inventors: William J. McAleer, Ambler; William M. Hurni; William J. Miller, both of North Wales, all of Pa.

[73] Assignee: Merck & Co. Inc., Rahway, N.J.

[21] Appl. No.: 31,712

[22] Filed: Apr. 20, 1979

[51] Int. Cl.³ .................. G01N 33/48; A61K 43/00; G01T 1/00

[52] U.S. Cl. .................. 424/1; 23/230 B; 424/1.5; 424/12

[58] Field of Search .............. 424/1, 12; 23/230 B; 260/112 B

[56] References Cited

U.S. PATENT DOCUMENTS

| | | | |
|---|---|---|---|
| 3,904,367 | 9/1975 | Golibersuch | 424/12 X |
| 3,979,509 | 9/1976 | Giaever | 424/12 |
| 4,024,235 | 5/1977 | Weetall et al. | 424/12 X |
| 4,034,072 | 7/1977 | Mtos et al. | 424/1 |
| 4,041,146 | 8/1977 | Giaever | 424/1 |
| 4,092,116 | 5/1978 | Giaever | 23/230 B |
| 4,113,712 | 9/1978 | Funakoshi | 424/12 X |
| 4,169,138 | 9/1979 | Jonsson | 424/12 |
| 4,189,464 | 2/1980 | Blumberg et al. | 424/1 |

OTHER PUBLICATIONS

Miller et al., Proc. Soc. Exp. Biol. Med., 149, 254–261 (1975).

Feinstone et al., Science, 182, 1026–1028 (1973).

*Primary Examiner*—Brooks H. Hunt
*Assistant Examiner*—Christine M. Nucker
*Attorney, Agent, or Firm*—Donald J. Perrella; Hesna J. Pfeiffer

[57] ABSTRACT

Liquid containing hepatitis A antibody is adsorbed on a surface. The surface is then coated with a proteinaceous material and incubated in the presence of the sample to form a complex of hepatitis A antigen and hepatitis A antibody. The complex is incubated again in the presence of excess radioactively labelled hepatitis A antibody, and the resulting radionuclide is measured.

4 Claims, No Drawings

ASSAY FOR HEPATITIS A ANTIGEN

BACKGROUND OF THE INVENTION

Presently known assays for detection of hepatitis A antigen in biological liquids consist of the immune adherence hemagglutination assay described by Miller et al., *Proc. Soc. Exp. Biol. Med.*, 149, 254-261 (1975) and the immune electron microscopic assay described by Feinstone et al., *Science*, 182, 1026-1028 (1973). Both of these methods are insufficiently sensitive to detect hepatitis A antigen in serum or plasma, and require a subjective evaluation to determine the end point.

OBJECTS OF THE INVENTION

It is, accordingly, an object of the present invention to provide an assay capable of detecting hepatitis A antigen in serum or plasma as well as other biological liquids. Another object is to provide an assay in which the end point is determined objectively. These and other objects of the present invention will be apparent from the following description.

SUMMARY OF THE INVENTION

Liquid containing hepatitis A antibody is adsorbed on a surface. The surface is then coated with a proteinaceous material and incubated in the presence of the sample to form a complex of hepatitis A antigen and hepatitis A antibody. The complex is incubated again in the presence of excess radioactively labelled hepatitis A antibody, and the resulting radionuclide is measured.

DETAILED DESCRIPTION

The present invention relates to an assay for hepatitis A antigen and, more particularly, to a highly sensitive radioimmune assay for hepatitis A antigen.

According to the present invention, a solution of hepatitis A antibody of known titer is adsorbed on a surface capable of adsorbing the antibody. The surface may be, for example, finely divided glass beads, or a plastic such as polyethylene, polypropylene, polystyrene or polyvinylchloride.

The adsorption conditions may be varied as to time, temperature, and concentration of the antibody. Typical adsorption conditions employ contacting the surface for at least about 2 hours, preferably for from about 8 to about 36 hours, at from above about 0° to about 60° with a solution of hepatitis A antibody of known titer. After the adsorption of the antibody the surface is coated with a material effective to be adsorbed by sites on the surface which are unoccupied by the antibody. Such a material is preferably a proteinaceous material, such as serum albumin, preferably bovine serum ablumin or human serum albumin. The coating may also be any non-proteinaceous chemical which is able to associate with the bead surface. This coating may be carried out under the same range of conditions employed to adsorb the antibody.

The coated surface is then incubated in the presence of the sample to be tested for hepatitis A antigen under conditions effective to form a complex of hepatitis A antigen and hepatitis A antibody. Typically this incubation takes from about 4 hours to about 48 hours or more at temperatures of from about 0° to about 45°.

After the complex is formed it is incubated with radioactively labelled purified hepatitis A antibody under conditions effective to attach the radioactively labelled purified hepatitis A antibody to the hepatitis A antigen portion of the hepatitis A antigen-hepatitis A antibody complex. This incubation typically requires from about 30 minutes to about 8 hours at a temperature of from about 25° to about 60°. The radionuclide residual is then measured in an appropriate counting device.

The following example illustrates the present invention without, however, limiting the same thereto. All temperatures are expressed in degrees Celsius.

EXAMPLE 1

A quantity (about 100) of polystyrene beads having a diameter of about 0.25 inch (0.64 cm) are placed in a 50 ml beaker. Hepatitis A antibody positive serum diluted 1:100 in physiologic saline containing 0.1% sodium azide (bacteriacide) is added in a quantity sufficient to cover the beads. A sheet of plastic is stretched over the top of the beaker which is then incubated at 5° for 24 hours. The supernatant liquid is decanted and the beads are placed in a 250 ml beaker to which 100 ml of saline azide (0.9% NaCl and 0.1% sodium azide in sterile distilled water) solution is added. The mixture is washed by slurrying for about 1 minute and the liquid then decanted. This slurry wash is repeated three more times. After the final wash the beads are transferred to a 50 ml beaker and 1% bovine serum albumin dissolved in saline azide solution is added in sufficient quantity to cover the beads. The beaker is allowed to stand at 5° for 24 hours. The liquid is decanted and the beads placed in a 250 ml beaker and slurry washed with saline azide solution four times as previously described. These washings are followed by two washes in distilled water. The beads are then placed on a sheet of filter paper and air dried for four hours at room temperature. The beads are then placed in a stoppered flask and stored at 20° until used.

Using 1.0 ml pipet, 1.0 ml of sample to be tested for hepatitis A antigen is placed in a 5 cm tube having an inside diameter of 0.8 cm. A coated bead is added and the tube is tapped to submerge the bead in the sample. The tube is sealed and incubated at room temperature overnight with continuous inversion of the tube. After incubation, the bead is washed with 2-5 ml amounts of distilled water. To the washed, damp beads 1.0 ml of radioactively labelled ($^{125}$I) hepatitis A antibody is pipetted into a 5 cm×0.8 cm tube. The tube is tapped to submerge the bead. The tube is covered and incubated 4 hours at 37° C. After incubation the bead is washed several times with 2-5 ml amounts of distilled water. The bead is then transferred into a counting tube and the radioactivity is counted in a Gamma counter.

What is claimed is:
1. An assay for detection of hepatitis A antigen in a sample which comprises the steps of:
   contacting a surface having hepatitis A antibody adsorbed thereto as the first layer with a proteinaceous material capable of being adsorbed to the surface;
   contacting the surface having adsorbed thereto the hepatitis A antibody and proteinaceous material with a sample containing hepatitis A antigen;
   incubating the surface under conditions effective to form a complex of hepatitis A antigen and hepatitis A antibody;
   incubating the surface in the presence of an excess amount of radioactively labelled hepatitis A antibody, and
   measuring the resulting radionuclide on the surface.

2. A hepatitis A antigen antibody radionuclide comprising a surface having adhered thereto as the first layer hepatitis A antibody, at least part of the antibody being complexed with hepatitis A antigen and at least part of the hepatitis A antigen being complexed with a radioactively labelled material.

3. A radionuclide according to claim 2 wherein the radioactively labelled material is hepatitis A antibody.

4. A diagnostic assay for hepatitis A antigen comprising a sample containing hepatitis A antigen and a surface having adsorbed thereto as the first layer hepatitis A antibody and a proteinaceous material.

* * * * *